United States Patent [19]

Bagby

[11] Patent Number: 4,936,848
[45] Date of Patent: Jun. 26, 1990

[54] IMPLANT FOR VERTEBRAE

[76] Inventor: George W. Bagby, 1111 W. 6th Ave. South #103, Spokane, Wash. 99204

[21] Appl. No.: 410,913

[22] Filed: Sep. 22, 1989

[51] Int. Cl.5 .............................................. A61F 2/44
[52] U.S. Cl. ...................................... 623/17; 623/18; 606/61
[58] Field of Search ............... 623/16, 17, 18; 606/60, 606/61

[56] References Cited

U.S. PATENT DOCUMENTS

| 4,328,593 | 5/1982 | Sutter et al. | 623/18 |
| 4,501,269 | 2/1985 | Bagby | 623/18 |
| 4,834,757 | 5/1989 | Brantigan | 623/16 |
| 4,865,604 | 9/1989 | Rogozmski | 623/18 |

OTHER PUBLICATIONS

Austenai Laboratories, Inc., Vitallium Surgical Appliances catalog, Mar. 1948.

*Primary Examiner*—Randall L. Green
*Assistant Examiner*—David H. Willse
*Attorney, Agent, or Firm*—Wells, St. John & Robert

[57] ABSTRACT

A surgical vertebral implant comprises a hollow rigid sphere having multiple fenestrations or openings leading to an interior cavity within which bone fragments can be positioned during surgery. It is useful in promoting arthrodesis (fusion) or arthroplasty (joint formation) between adjacent spinal vertebrae. The procedures for implantation require formation of complementary spherical bony recesses between adjacent vertebrate, placement of the spherical implant, positioning of bone fragments within the implant, and post-operative treatment of the patient consistent with the intended surgical result (fusion of joint formation).

16 Claims, 3 Drawing Sheets

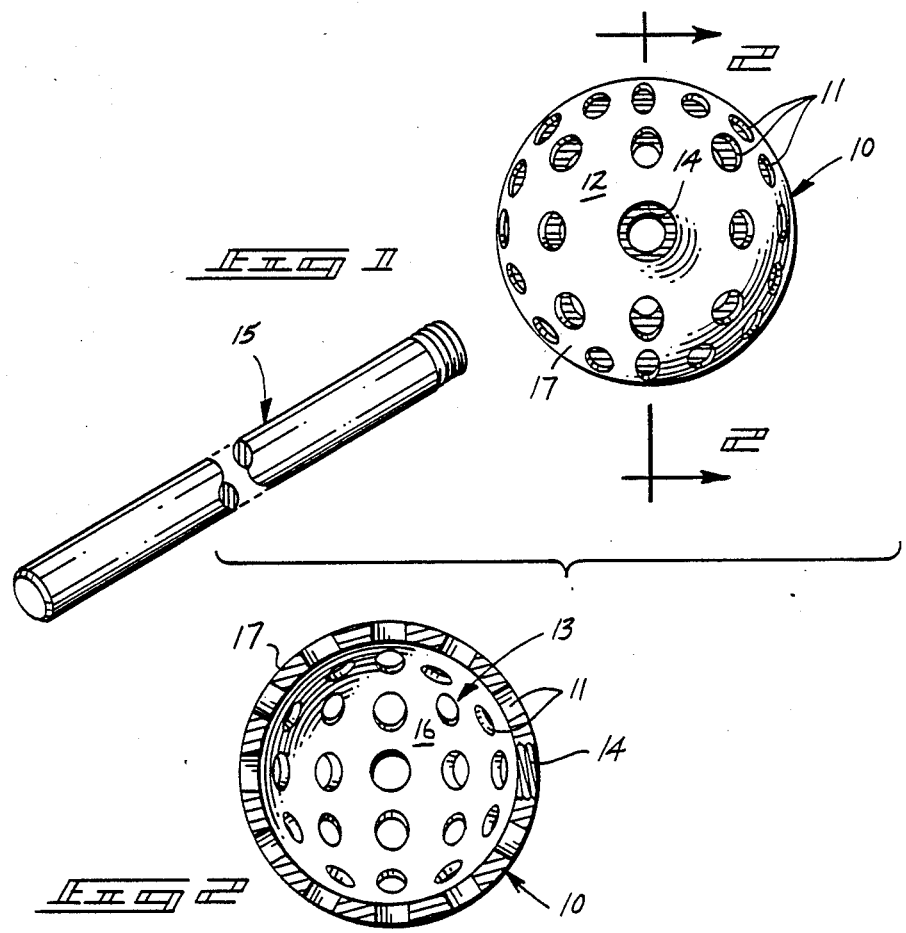
Fig. 1
Fig. 2
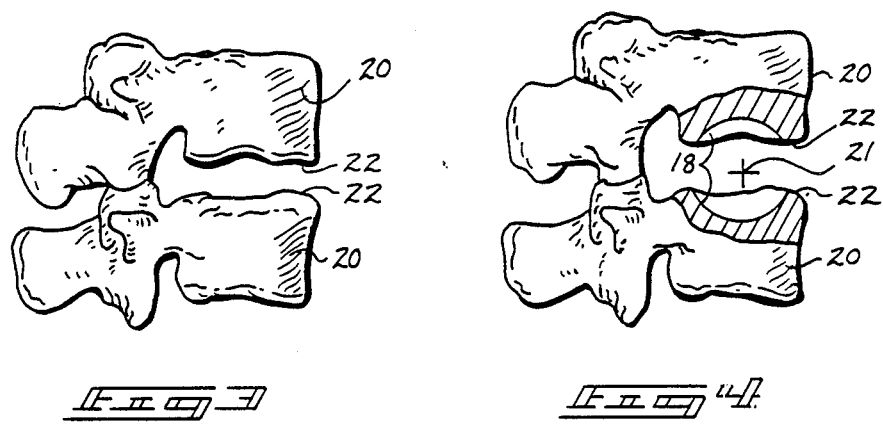
Fig. 3
Fig. 4

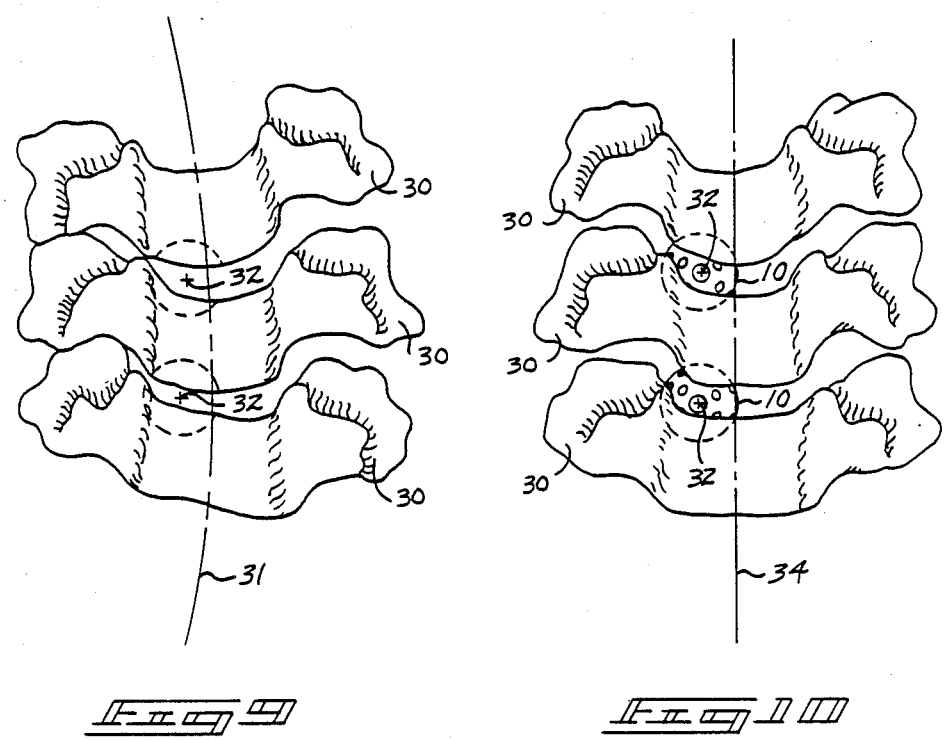

4,936,848

IMPLANT FOR VERTEBRAE

TECHNICAL FIELD

This disclosure relates to implants for the vertebral comumn, and specifically to an implant capable of alternately selectively achieving arthrodesis (fusion) or arthroplasty (joint formation) between adjacent vertebrae.

BACKGROUND OF THE INVENTION

The vertebral column is a flexible spinal column, extending along the back of vertebrate animals, which includes a series of bones termed the vertebrae. The major function of the vertebral column is protection of the spinal cord. It also provides stiffening for the body and attachment of the pectoral and pelvic girdles and many muscles. In humans an additional function is to transmit body weight in walking and standing. Each vertebra, in higher vertebrates, consists of a ventral body, or centrum, surmounted by a Y-shaped neural arch. This arch extends a spinous process or projection downward and backward that may be felt as a series of bumps down the back, and two transverse processes, one to either side, which provide attachment of muscles and ligaments. The centrums are separated by cartilaginous intervertebral disks, which help cushion shock in locomotion.

In general, these disks have two functions: to allow movement between pairs of vertebrae and to act as buffers against the shocks of running, jumping, and other activities that apply stresses to the spine. The disks also cooperate with paired synovial joints, one on each side of the vertebral arch, to facilitate complex multidimensional relative movement between adjacent vertebrae.

Surgical intervention is often required following degeneration of intervertebral disks. In many instances, spinal fusion is the desired result. The usual rationale for fusion is prevention of progressive apposition of the vertebral bodies with consequent subluxation of the facet joints, narrowing of the nerve route foramina, and development of arthrosis. For the most persistent cases of disabling back pain, direct bony fusions are often performed to stop the painful motion between vertebrae by permanently locking them to one another. However, in many cases it might be advisable to allow continued movement between adjacent vertebrae, which helps to prevent mechanical breakdown at nearby bone segments.

When dealing with ruptured disks, one surgical remedy is to partially remove the disk. Such removal satisfies only one particular part of the problem by removing the displaced disk material that has created pressure on a spinal nerve, but it does not restore the disk to its normal configuration. The result is a flattened and degenerative disk, which is usually accompanied by arthritis of the facet joints and might result in persistent low back pain. This might also lead to recurrent pressure on a nerve because the disk thinning associated with degeneration might lead to formation of a spur that results in renewed pressure on the nerve. Current fusions operations or bony decompressions are utilized, but they are only relatively satisfactory procedures because of the magnitude of any fusion operation and because spurs tend to recur when removed without an arthrodesis. Accordingly, there is a tendency for stenosis of the spinal canal or neural foramen to occur.

The present invention was developed in an effort to provide a surgeon with an element of control over the end result of such operations following disk removal. The desired result can be either arthrodesis (fusion) or arthroplasty (joint formation). Furthermore, recognizing that all surgical procedures will fail to achieve their intended results in a statistical percentage of situations, the present invention assures that an acceptable result will be achieved as an alternative to that desired. Briefly, where arthrodesis is the intended result, arthoplasty will be the alternative result, and where arthroplasty is the intended result, arthrodesis will be the alternative result. Thus, even though a planned fusion does not occur, the patient will be provided with a useful prosthetic joint between the affected vertebrae and, conversely, where joint formation was intended and not achieved, an acceptable solid fusion will be achieved in its place.

U.S. Pat. No. 4,501,269, issued on February 26, 1985, discloses an apparatus and process for immediate stabilization and subsequent promotion of fusion in bone joints. The disclosed implant is a metal cylinder or basket having fenestrations arranged about its cylindrical surface. Bone fragments are utilized within the basket to promote bone growth through the basket. While a cylindrical implant has limited usefulness in spinal operations where fusion is desired, the placement of a cylindrical basket is difficult because of the amount of surrounding bone that must be removed in order to properly insert the cylindrical object between adjacent vertebrae.

Recognition of the limitations relating to fusion procedures has led to identification of a need for an immediate artificial disk or fusion operation that can be done in the process of removing the disk to prevent further disk space narrowing and degeneration. It is this narrowing or loss of a shock absorber between adjacent vertebrae that leads to facet joint hypertrophy, spur development, etc. Furthermore, the required surgery should be of lower magnitude than present fusion surgery and should result in more predictably acceptable results. For example, present fusion operations require an additional one to two hours for carrying out the surgery after removal of the disk, and also require additional incisions to collect the required bone, unless a bone bank is utilized. Six to 12 months' time is needed for the fusion to become solid and this operation carries a 10 to 20 percent failure rate wherein pseudoarthrosis (evidenced by an unplanned, false joint) is the end result.

The present development is designed to meet the needs of a surgeon intending to produce either a multidirectional joint or a bony fusion, and provides the benefit of an acceptable alternative surgical result where the intended surgery fails. It assures immediate spacing of the vertebrae to remove verve pressure and an implant that can promote either arthrodesis or arthroplasty as indicated by the situation of a specific patient. This is accomplished by spreading of the vertebrae and implantation of a hollow spherical member having an interior cavity that can be filled with bone fragments and having an exterior wall with multiple fenestrations leading to the cavity. By selective choice of surgical procedures, the surgeon can promote fusion through the implant or tissue growth about it to form a defined joint. While one of these results may be the intended goal of surgery; the other, if it occurs, can be an acceptable alternative.

BRIEF DESCRIPTION OF THE DRAWINGS

The preferred embodiment of the invention is illustrated in the accompanying drawings, in which:

FIG. 1 is an enlarged perspective view of a spherical implant;

FIG. 2 is a cross sectional view through the spherical implant taken along line 2—2 of FIG. 1;

FIG. 3 is a diagrammatic side view of a pair of adjacent spinal vertebrae;

FIG. 4 illustrates formation of bony recesses in the vertebrae;

FIG. 9 is a diagrammatic posterior view illustrating selection of locations for placement of spherical implants to correct a scoliotic curve; and FIG. 10 schematically illustrates placement of spherical implants to correct the curve shown in FIG. 9.

DETAILED DESCRIPTION OF THE PREFERRED EMBODIMENT

Figure 5:
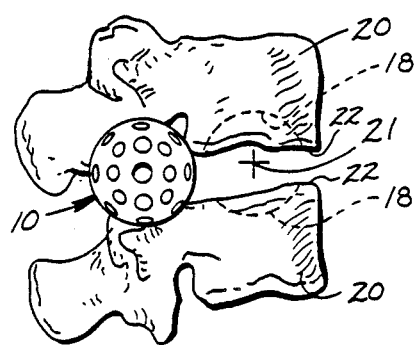
FIG. 5 illustrates initial spread of the vertebrae during placement of the spherical implant.

The following disclosure of the invention is submitted in compliance with the constitutional purpose of the Patent Laws "to promote the progress of science and useful arts" (Article 1, Section 8).

The present disclosure pertains to a spherical implant and to a method of utilizing the spherical implant by placement between opposing vertebrae in a spine to selectively promote arthrodesis (a fused connection) or arthoplasty (a joint). In humans, the device is designed to be used mainly in the lumbar spine. Such usage is normally dictated by the existence of a ruptured disc or degenerative disc pathology. Usage of the disclosed spherical implant is also applicable to the thoracic and cervical areas of the spine.

The implant comprises a hollow sphere 10 having an outer wall 12 surrounding an interior cavity 13. A plurality of fenestrations 11 are formed through the outer wall 12 of the sphere 10 in open communication with its cavity 13.

The design of sphere 10 provides the surgeon with control over which end result (arthrodesis or arthroplasty) is to be encouraged.

If an arthrodesis or fusion is more desirable, then a relatively larger implant should be used when compared to the prepared bed, thus stretching the annulus to an extreme for better immobilization. Under those circumstances, as much bone as is available is inserted into the implant as the increased amount of bone graft material is a stronger stimulus for osteoblastic activity and therefore bone fusion. Post-operatively the patient would be treated with a formidable support to the back to assist in immobilizing it and therefore encouraging the fusion process. Time of fusion would have to be determined by x-ray.

If an arthroplasty is more desirable, then a smaller implant relative to the bed size is used, resulting in minor or only physiological stretch of the annulus and little or no bone is placed in the implant. Post-operatively a light brace is used for discomfort only and time of fusion less critical as far as follow-up x-rays are concerned. Statistically, some vertebrae will fuse and some will not, regardless of the techniques carried out.

The hollow sphere 10 can be made of metal or another material, such as ceramics, which is biocompatible with the adjacent body tissue and sufficiently rigid to withstand the compressive forces between adjacent spinal vertebrae. The exterior surface areas of sphere 10 that surround the fenestrations 11 are smooth and otherwise uninterrupted. The diameter of sphere will vary widely, typical sizes being in the range of 11, 13, 15, and 17 mm.

An enlarged window or opening 14 is formed through the wall 12 of sphere 10 in open communication with its cavity 13. A typical size diameter for opening 14 is approximately 5 mm. Opening 14, which might be threated, is used as an attachment means to releasably mount one end of a driver or handle 15, that serves as a tool to facilitate placement of sphere 10. While a straight handle 15 is illustrated in FIG. 1, other handle configurations can be utilized as required for specific surgical needs. For instance, a curved handle might be required in order to properly work the sphere 10 into position through the bone structure adjacent to the surgical site.

The opening 14 is also utilized as an enlarged aperture leading to the interior cavity 13 for the introduction of bone chips or other materials into cavity 13 within sphere 10. It might further be used in association with a removable of threaded cover, but normally will remain in an open state after surgical implantation.

The cavity 13 within sphere 10 is defined by a spherical inner surface 16 that is concentric with its outer surface 17. The difference in diameters between the outer surface 17 and inner surface 16 is substantially less than the diameter of the outer surface 17 (see FIG. 2).

The fenestrations 11 formed through sphere 10 are preferably circular openings centered about axes intersecting the center of the sphere. The diameter of each opening is substantially less than the diameter of the sphere. A typical diameter size for fenestrations 11 is approximately 2-3 mm.

Figure 8:
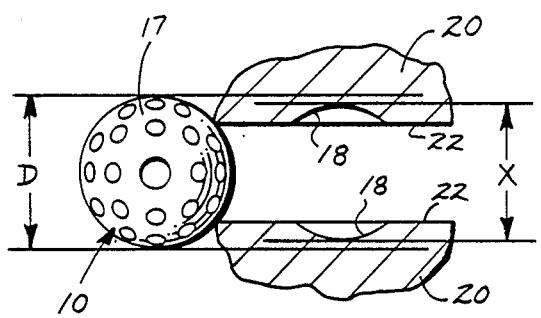
FIG. 8 is a diagrammatic view illustrating the geometry of the spherical implant and bony recesses.

The sphere 10 is adapted to be located between bony recesses 18 formed in opposed facing surfaces of a pair of adjacent spinal vertebrae 20 following removal of a ruptured, flattened or degenerated disc (not shown). The exterior diameter of sphere 10 is slightly greater than the diameter of the bony recesses 18 between which it is to be located (see FIG. 8).

The present method for selectively promoting arthrodesis or arthroplasty between vertebrae 20 can best be understood from a study of FIGS. 3-7.

First, the operating surgeon must partially or completely remove a ruptured, flattened or degenerated disc (not shown) located between the centrums of a pair of adjacent vertebrae having opposed facing surfaces (FIG. 3). The illustrated separation between the opposed facing surface 22 in FIG. 3 is less than it should be due to disc degeneration which has occurred.

Next, the surgeon must separate the vertebrae, which will typically be accomplished by use of a lamina spreader (FIG. 4). The surgeon then selects a desired center of motion between the opposed facing surfaces on the pair of vertebrae 20. In FIGS. 4-7, the selected center of motion is visually indicated at 21.

The next step involved in the present method requires drilling and/or reaming the facing surfaces of the pair of vertebrae to form opposed body recesses centered about the selected center of motion 21. The bony recesses 18 are illustrated in a partial section shown in FIG. 4.

Figure 6:
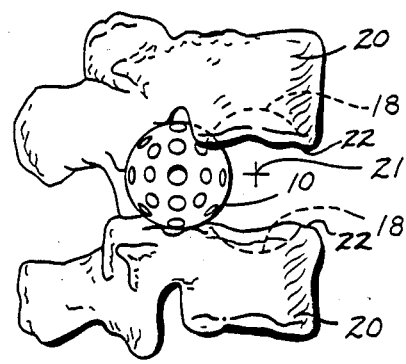
FIG. 6 illustrates continued movement of the spherical implant toward the receiving bony recesses.
Figure 7:
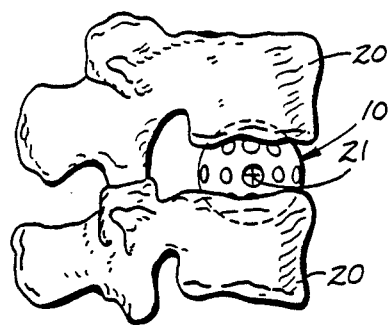
FIG. 7 illustrates placement of the spherical implant in the bony recesses.

FIGS. 5, 6 and 7 illustrate sequential placement of sphere 10 in a position coincident with the selected center of motion 21. This is accomplished by progressively moving sphere 10 into a location between the bony recesses 18. Such placement will require spreading of the vertebrae 20 in order to facilitate entrance of the sphere 10 between them.

While not shown in FIGS. 5-7, a driver or handle attached to sphere 10 will normally be utilized to facilitate its placement. Handle 15 serves as a driving tool to assist in controlling movement of sphere 10 prior to its being seated between the bony recesses 18.

The implanted sphere 10 will be held in place between the bony recesses 18 by the surrounding fibers and muscle (not shown) that complete the spinal structure. Due to the relative sizes of the spherical implant and bony recesses, the sphere 10 separates the adjacent vertebrae 20 by a distance greater than their relative positions prior to surgery. In all instances, the diameter of the bony recesses 18 (shown as X in FIG. 8) will be less than the exterior diameter of the outer surface 17 about sphere 10 (shown as D in FIG. 8). The difference in diameter will result in spreading of the vertebrae 20 from their original pre-operative positions. This causes the elastic nature of the surrounding tissue and muscles to maintain the sphere 10 in compression between the vertebrae 20.

When being used to promote arthrodesis, sphere 10 should be packed with bone chips or fragments (not shown) to encourage bone growth through the fenestrations 11. Additional bone fragments should be packed about the exterior of the implanted sphere 10. The bone fragments are preferably autogenic, since those produced during the forming of the bony recesses 18 will be most effective in promoting subsequent bone growth. The use of autogenic bone fragments in a related surgical procedure is described in U.S. Pat. No. 4,510,269, which is hereby incorporated into the present invention disclosure by reference. The application of this technique to the present spherical implant will be readily understood by those skilled in this field.

It is preferably to place some bone fragments within sphere 10 even when an arthroplasty is anticipated. While the presence of bone materials within the implant is primarily to promote arthrodesis, it will result in a process of healing in the vicinity of the spherical implant that creates a different type of arthroplasty (pseudoarthrosis) than if no healing had taken place in the total absence of bone within the implant. It has been noted, in situations where attempted fusions have failed, that the operational area sometimes fills in with scar tissue instead of bone or will have less scar tissue than planned. This results in production of a synovial lining having fluid in it, which more closely resembles a true joint. Simply placing an empty metal implant into the body would normally be expected to produce no stimulation for a healing process and no bodily reaction leading to arthroplasty or arthrodesis. Such implantation would therefore be less likely to be physically desirable and the end result is less likely to resemble a true joint.

A novel aspect of this invention is the ability given to the surgeon to selectively promote either arthrodesis or arthroplasty between adjacent spinal vertebrae.

When arthrodesis (fusion) is the desired result, the sphere 10 and the available open spaces about it should be packed with bone chips and/or other materials that tend to promote bone growth into and through the spher, such as hydroxyapatite. When arthroplasty (joint) is desired, the interior of sphere 10 should contain less bone material and fibrous union or healing will usually take place about the outer spherical surface areas between the fenestrations 11 of the sphere 10.

The difference between the exterior diameter of the sphere 10 and the diameter of the bony recesses 18 between which it is to be located should be substantial when arthrodesis is the desired result, and should be minimal when arthroplasty is desired. It is to be noted that the less spread or difference in diameter of bony recess compared to the outside diameter of the implant, the better the congruity and facilitation of motion about the center of sphere 10. Conversely, discongruity will encourage fusion. As an illustrative example only, when utilizing a sphere that is 17 mm in diameter, a reamer diameter of 14 mm might be used to promote arthrodesis, while a reamer diameter of 16 mm might be used when arthroplasty is the desired result. In both instances the compressive forces of the surrounding tissues and muscles will cause the bony recesses to spread sufficiently to properly seat the spherical implant between them in surface-to-surface contact.

The post-operative regimen of the patient will also affect the end result desired in a particular situation. Where arthrodesis is desired, the affected ares must be immobilized for a time sufficient for fusion of bone to occur. This might require wearing of a brace for six months. Conversely, arthroplasty is more likely when joint movement is encouraged by minimizing support of the operative area and encouraging gradual increase in normal activities.

It should be recognized that in any implant situation, instances of "failure" will always occur. With the present implant, such "failure" will result in an acceptable bodily condition. If bone mass grows through the sphere 10 in situations where arthroplasty was the desired result, the patient will have a fusion between the adjacent vertebrae which will immobilize the vertebrae and not require subsequent treatment or surgery. Similarly, if bone growth does not occur through the sphere 10 where arthrodesis was the desired result, sphere 10 will be covered by fibrous growth to produce a spherical socket and a definable spherical joint between the adjacent vertebrae which will maintain their relative positions during limited movement or the vertebrae.

Thus, the implant has the ability to turn "failure" of intended surgical procedures to a "successful" result that does not require corrective steps. The end result of such an implant is not truly random in nature, because the implant and its method of use provides the surgeon with parameters that can be selected to promote arthrodesis or arthroplasty as the intended result of implantation, even though the alternative result will be acceptable in most instances.

A suitable surgical technique for utilizing the spherical implant will be detailed below. It is subject to substantial variation, depending upon the many variables encountered in surgical situations. Accordingly, this discussion should be viewed as merely exemplary.

When using a conventional posterior approach, the patient is placed prone on an appropriate frame for carrying out low back surgery under general anesthesia. A mid-line incision is made dorsally and the usual approach for laminectomy and disc removl is carried out. A lamina spreader is utilized and the center of disc motion is approached with a probe, including use of an x-ray check on the table.

A bed is drilled and/or reamed and the bone chips harvested. The selection of a spherical reamer will require one of appropriate size which would be approximately equal to the size of the utilized implant for encouraging arthoplasty and a slightly smaller reamer (when compared to the spherical implant) when encouraging arthrodesis. The overall operation for arthrodesis should be of larger magnitude and size. The forming of the bony recesses 18 should be developed by use of progressively enlarged reamers to approach the final size, with care being taken to assure that the reaming takes place equally in each adjacent vertebra. The drills and/or reamers can be rigid or flexible, as well as straight or curved, depending upon specific surgical needs in each instance of use.

Bone chips and fragments produced during drilling and reaming should be separated from the cartilage and disc material and the bone only returned to the implant. Bone may also be utilized from the lamina or spinous process if needed, as well as from external sources, such a bone bank.

A special driver or handle 15 is screwed into the receiving threaded window or opening 14, which might be approximately 5 mm. in diameter, and is tapped into place. This larger single fenestration is also utilized for filling the implant with bone. After an appropriate check for position and hemostasis the driver or handle 15 is unscrewed to remove it and the wound should be irrigated and closed in the usual fashion, taking local and general measured for antisepsis.

An alternative surgical route is anterior implantation. This will require abdominal access (intra or extra peritoneal) for the lumbar region, transthoracic access for the thoracic vertebrae, and anterior lateral access for the cervical levels. The anterior lumbar approach may be used when the posterior approach is contraindicated, and would be the usual approach in thoracic or cervical applications. Anterior implantation makes possible the use of larger spherical implants, but the above-described implantation procedures will otherwise remain unchanged. One advantage of the anterior approach in the lumbar area is that proper centering of the implant might be easier, but in most instances the posterolateral procedure will be more practical.

FIGS. 9 and 10 schematically illustrate usage of the implant to correct a scoliotic curve between adjacent vertebrae 30. The scoliotic curve is illustrated by dashed line 31. Correction can be accomplished by selecting locations for the center of motion 32 between the adjacent vertebrae 30 which are laterally offset from the curve 31. Illustrative selected centers of motion 32 are shown for bony recesses 33 formed in the opposing surfaces of vertebrae 30 as previously described. FIG. 10 illustrates the vertebrae 30 after placement of implanted spheres 10 between them, the center of each sphere being coincident with the previously selected centers of motion 32. The eccentric placement of the spheres 10 has laterally straightened the vertebrae 30 along the center line shown at 34.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. An implant for selectively promoting either arthrodesis or arthroplasty between adjacent spinal vertebrae, comprising;
   a hollow sphere having an outer wall surrounding an interior cavity, the sphere being adapted to be located between bony recesses formed in opposed facing surfaces a pair of adjacent spinal vertebrae following removal of a ruptured, flattened or degenerated disc;
   a plurality of open fenestrations formed through the outer wall of the sphere in communication with the cavity to provide openings through which bone can grow into and through the sphere to promote arthrodesis, separated by outer spherical surface areas between the fenestrations about which fibrous union or healing can take place to promote arthroplasty.

2. The implant of claim 1, further comprising:
   attachment means on the sphere for temporarily securing it to a tool used to locate the sphere between opposed bony recesses formed about a selected center of motion between prepared surfaces of adjacent spinal vertebrae.

3. The implant of claim 2, wherein the attachment means comprises:
   a handle; and
   a complementary opening in the sphere through which one end of the handle can be releasably secured to facilitate placement of the sphere by manipulating the attached handle.

4. The implant of claim 1, wherein the hollow sphere is made of rigid material capable of withstanding compressive forces between adjacent spinal vertebrae without deformation.

5. The implant of claim 1, wherein the exterior diameter of the sphere is slightly greater than the diameter of the bony recesses between which it is to be located.

6. The implant of claim 1, further comprising:
   an enlarged opening formed through the outer wall of the sphere through which bone fragments can be inserted into the cavity to promote bone growth following its placement.

7. The implant of claim 1, wherein the exterior surface areas of the sphere surrounding the fenestrations are smooth.

8. The implant of claim 1, wherein the cavity within the sphere is defined by a spherical inner surface concentric with its outer surface.
   the difference in diameters between the outer and inner surfaces of the sphere being substantially less than the diameter of its outer surface.

9. The implant of claim 1, wherein the fenestrations are circular openings centered about axes intersecting the center of the sphere;
   the diameter of each opening being substantially less than the diameter of the sphere.

10. A method for selectively promoting arthrodesis or arthroplasty between adjacent spinal vertebrae, comprising the following steps:
    partially or completely removing a ruptured, flattened or degenerated disc located between a pair of adjacent vertebrae having opposed facing surfaces;

separating the pair of vertebrae by use of a lamina spreader;

selecting a desired center of motion between the opposed facing surfaces on the pair or vertebrae;

drilling and/or reaming the facing surfaces of the pair of vertebrae to form opposed bony recesses centered about the selected center of motion; and placing the center of a fenestrated hollow sphere in a position coincident with the selected center of motion by locating it between the bony recesses so that either (a) bone can subsequently grow into and through the sphere to promote arthrodesis or (b) fibrous union and/or healing can subsequently take place about the smooth spherical surface areas of the sphere to promote arthroplasty.

11. The method of claim 10, further comprising the intermediate step of attaching a driving tool to the sphere prior to its placement.

12. The method of claim 10, wherein the step of drilling and reaming the pair of vertebrae involves forming opposed partial spheroidal bony recesses between the opposed facing surfaces of the pair of vertebrae, the exterior diameter of the sphere being slightly greater than the diameter of the opposed bony recesses in the vertebrae.

13. The method of claim 10, comprising the following additional step:

inserting bone fragments into a cavity within the sphere to encourage bone growth through its fenestrations following placement of the sphere between the bony recesses.

14. The method of claim 10, comprising the following additional step:

inserting bone fragments produced during the forming of the bony recesses into a cavity within the sphere to encourage bone growth through its fenestrations following placement of the sphere between the bony recesses.

15. The method of claim 10, wherein arthrodesis is promoted by:
 (a) packing the hollow sphere with bone material;
 (b) utilizing a substantial diameter difference between the interiors of the bony recesses and the exterior of the sphere; and
 (c) subsequently immobilizing the affected surgical area to permit fusion to occur.

16. The method of claim 10, wherein arthroplasty is promoted by:
 (a) placing bone material within the hollow sphere without packing;
 (b) utilizing a minimal diameter difference between the interiors of the bony recesses and the exterior of the sphere; and
 (c) subsequently encouraging joint movement by minimizing support of the operative area and gradually increasing normal activities to permit formation of a joint to occur.

* * * * *